United States Patent [19]
Bade

[11] Patent Number: 4,958,011
[45] Date of Patent: Sep. 18, 1990

[54] ESTER-STABILIZED CHITIN

[76] Inventor: Maria L. Bade, Four Bowser Rd., Lexington, Mass. 02173

[21] Appl. No.: 820,247

[22] Filed: Jan. 17, 1986

Related U.S. Application Data

[63] Continuation-in-part of Ser. No. 622,128, Jun. 19, 1984, abandoned, which is a continuation-in-part of Ser. No. 508,476, June 7, 1983, abandoned.

[51] Int. Cl.$^5$ .............................................. C08B 37/08
[52] U.S. Cl. ...................................................... 536/20
[58] Field of Search ............................ 536/20; 514/55

[56]  References Cited
U.S. PATENT DOCUMENTS

| | | | |
|---|---|---|---|
| 2,689,244 | 9/1954 | Jones | 536/20 |
| 3,903,268 | 9/1975 | Balassa | 514/55 |
| 4,286,087 | 8/1981 | Austin et al. | 514/55 |
| 4,293,098 | 10/1981 | Muralidhara | 536/20 |

FOREIGN PATENT DOCUMENTS

| | | | |
|---|---|---|---|
| 0059700 | 5/1978 | Japan . | |
| 0139101 | 8/1982 | Japan | 536/20 |

OTHER PUBLICATIONS

Kaifu et al., Polymer Journal, Studies on Chitin, V. Formylation, Propionylation, and Butyrylation of Chitin, vol. 13, No. 3, pp. 241–245 (1981).
Kaifu et l., Chemical Abstracts, vol. 95, 1981 No. 82619g.

Primary Examiner—Johnnie R. Brown
Assistant Examiner—Elli Peselev

[57] ABSTRACT

Ester-stabilized chitin polymers which have been dissociated and purified from a naturally occurring calcified chitin/protein matrix, and which substantially retain the structural features of the chitin matrix in that they comprise elongated fibers which are rapidly and quantitatively recognized by enzymes specific for naturally occurring chitin. The chitin polymers are made by a method in which the naturally occurring matrix is first decalcified and deproteinized, and then the chitin is dispersed and stabilized in a cold dilute ester-forming acid before being recovered. The polymers are useful in processes requiring consistent, reproduceable structure. Polymers having these useful attributes are particularly identifiable by their ability to react with enzymes specific for naturally occurring chitin.

9 Claims, 3 Drawing Sheets

ESTER-STABILIZED CHITIN

BACKGROUND OF THE INVENTION

This application is a continuation-in-part of my copending application USSN 622,128 filed June 19, 1984, now abandoned which in turn was a continuation-in-part of my earlier application USSN 508,476, filed June 27, 1983, now abandoned. Both of my above earlier applications are hereby incorporated by reference.

This invention relates to polymeric derivatives of naturally occurring chitin and to methods for making and using those derivatives.

Chitin refers to carbohydrate polymers of N-acetylated glucosamine monomer units synthesized in nature in plentiful supply, e.g., as part of the skeleton or shell of crustaceans and other arthropods, of mollusks, or in the walls of fungal cells. Naturally occurring chitin performs an exceedingly wide variety of architectural functions.

Chitin's naturally occurring structure provides an unusual combination of properties including high tensile strength, toughness, bioactivity, biodegradability, and non-immunogenicity. A wide range of industrial uses has been suggested for chitin or its deacylated derivative, chitosan. [See, e.g., Muzzarelli, Chitin (1977) Pergamon Press, New York, N.Y. at pp. 207-265; Austin et al. (1981) Science 212: 749-753; and Rawls (1984) Chemical & Engineering News, May 14, pp. 42-45]. While the estimated yearly biomass production of chitin ($10^{11}$ tons) is comparable to that of cellulose, its industrial promise generally has not been realized until now, because of severe problems with quality control, which arise from purification procedures. Chitin from the most readily available sources, e.g., crustacean carapaces, occurs in intimate association including covalent bonding with other materials, such as protein, minerals (chiefly in form of calcium salts), lipids, and coloring matter (including carotenes). Such extraneous matter generally must be removed prior to final preparation of chitin. Additionally, recovery and purification of useful chitin products has been hindered by the difficulty of dispersing or dissolving chitin in all but strong mineral acids or exotic anhydrous solvents.

Two basic purification strategies have been used, which occasionally are combined. First, the chitin may be subjected to drastic purification conditions which, because it was thought that chitin is chemically inert, were an attempt to dissolve all other material away from the chitin. Second, chitin has been subjected to mechanical attack to break the chitin into very small particles and thereby disintegrate the structure in hopes of exposing functional portions of the chitin/protein matrix. Occasionally, chemical attack is first used to aid the mechanical disintegration. Examples of these two approaches are given below.

These strategies typically suffer either from incomplete removal of undesired materials such as minerals or proteins, or drastic alteration of chitin structure in unpredictable, non-reproduceable ways that may destroy desirable chitin properties and render the product useless in many applications.

While considerable attention has been paid to chemical modification of various chitin-derived materials, the quality and preparation of the starting material used for such modifications often has been ignored entirely. For example, the starting material is typically referred to as "commercially available carbonate-free chitin" [Vogler U.S. Pat. No. 2,831,851], "purified chitin" [Jones U.S. Pat. No. 2,689,244], or "crude chitins... commercially available" [Stacey & Webber, Methods in Carbohydrate Chemistry, Vol. I, p. 228 ].

Specifically, for example, Jones U.S. Pat. No. 2,689,244 has no disclosure of the method of purifying chitin. An unspecified starting material is subjected to harsh sulfating conditions to render the product water soluble, presumably by sulfation at a substantial percentage of available sites and/or by hydrolysis to reduce molecular weight. Exemplary harsh conditions include subjecting the material to sulfur trioxide in basic organic liquids at 70°-110° for 2-25 hours. There is no indication that the material being sulfated (much less the resulting sulfated product) has any fine structure, or that either serves as a substrate for chitin-specific enzymes.

Where a disclosure of the method used to obtain purified chitin is provided, it may be characterized as a "well-known procedure". Muzzarelli (pp. 89 et seq.) provides a comprehensive review of various techniques that have been used for preparing chitin from raw material. BeMiller (1965) Methods Carbohydrate Chem. V. "Chitin", pp 103-105 also reviews chitin preparations. Such preparations typically include crushing or milling to disperse the raw material in an aqueous solution, deproteinizing with hot concentrated alkali, and decalcifying with hydrochloric acid. In some cases the resulting material is then subjected to harsh oxidation during purification, for example by $KMnO_4$, $H_2O_2$, or ozone. See, for example, Berger et al. (1958), Biophys Biochem. Acta, 29: 522-534.

In an effort to recover "active" chitin, a later researcher (Muralidahara U.S. Pat. No. 4,293,098) discloses a "mechanical" (non-chemical) chitin recovery process. Shellfish waste is dried and ground to remove the meat adhering to the shell and to aid separation of heavier materials from the chitin. The process involves grinding to an extremely fine particle size of between 10 and 400 microns (2:8), and the resulting material (which Muralidahara calls "active chitin") contains structural protein co-valently bound with the chitin, as well as some calcium based materials (2:37-40). Muralidahara avoids sulfation and mentions it only as background art. Moreover, Muralidahara gives no indication that the so-called "active chitin" can be dispersed in water, or that chitin-specific enzymes recognize and act on it as a substrate.

McCandliss, U.S. Pat. No. 4,536,207 discloses a method of producing small (less than 0.5 mm) particles from shell-fish waste. The particles contain at least 50% protein.

Apart from Muralidahara and McCandliss, where an attempt has been made to preserve some characteristic or other of naturally occurring chitin, the prior art ultimately has been forced to resort to relatively harsh conditions in order to disperse the chitin, as repeatedly acknowledged in the quotations given below.

One researcher approached the problem by trying to dissolve "commercial chitin" (of unknown origin) in acid systems such as trichloracetic/formic acid [Austin U.S. Pat. No. 3,892,731] or in a combination of a chloroalcohol [e.g. chloroethanol] and a mineral acid (e.g. HCl, $HNO_3$, $H_2SO_4$, or $H_3PO_4$) [Austin U.S. Pat. No. 3,879,377].

In later work, the same researcher turned to other solvents such as dimethylacetamide, N-methylpyrrolidone or mixtures thereof with an admixture of lithium chloride, because the procedures disclosed in the above-mentioned '731 and '377 patents provide "solutions which are not as stable as desired for storage for considerable lengths of time." [Austin U.S. Pat. No. 4,059,457].

In yet another approach [Austin et al. U.S. Pat. No. 4,029,727], the goal is stated to be "a solution of chitin in which the chitin is fully dissolved or dispersed, and without order or organization." To that end, red crab chitin is dissolved in solvent systems comprising trichloroacetic acid, chloralhydrate, and methylene chloride.

Finally, Austin et al. U.S. Pat. No. 4,286,087 proposes a process for treating chitin to make it easier to store and ship, while preserving the levo(-)optical rotation said to be beneficial in uses such as wound healing and supposedly characteristic of naturally occurring chitin. The process includes boiling chitin (e.g. from brown shrimp) for 1½ hours in a mixture of 85% $H_3PO_4$ and 2-propanol. Austin et al. (1981) Science 212: 749–752 discloses a similar procedure for making a redispersible chitin powder in which a chitin slurry is boiled for two hours in 85% $H_3PO_4$ and 2-propanol, dispersed in water, sheared, and freeze-dried. Austin's aim is to produce a material that is "hydrolyzed" to a desired lower molecular weight. The phosphoric acid is said to be "held in the form of a phosphate salt by several free amine groups, since exhaustive water extraction and attempted elution with aqueous hydrochloric acid reduced the phosphorus content to 0.1 percent." The material is dried as a powder.

Another research group has taken various approaches to the problem of recovery of useful material from naturally occurring chitin/mineral/protein matrices.

Peniston U.S. Pat. No. 3,533,940 discloses preparing chitosan from crab shell by treating the shell with HCl, deproteinizing and treating it with permanganate and oxalic acid, following which the chitin is partially deacetylated with 40% caustic soda at 150° C. Peniston et al. U.S. Pat. No. 4,066,735, discloses decalcification using excess sulfurous acid, said to be preferable to HCl since the latter is relatively expensive and hazardous, and may be so strong as to "cause some degradation of chitin during demineralization treatment." Sulfurous acid is also said to be preferable to sulfuric acid because the latter is said to produce calcium sulfate which is insoluble and precipitates in the interstices and on the surface of shell particles. The decalcification process is said to be appropriate either before or after protein removal.

In another approach, Peniston et al. [U.S. Pat. No. 4,199,496] discloses a process for treating shells to recover their various constituents by first boiling the shells in sodium hydroxide to extract protein, and then subjecting the residue to mineral acid such as HCl.

Many other chitin purification techniques have been published in addition to those specifically mentioned above. In sum, chitin purification techniques generally proceed on the assumption that harsh treatments are necessary to solubilize and remove the unwanted material; when mentioned at all, the specific methods used to disperse the chitin after removing such material are not designed to preserve and/or stabilize the innate structure. The result is that native chitin structure and its advantages are lost, and that the altered chitin product is often so variable as to be of little value.

Chitin preparations from calcium-bearing sources by existing methods yield material which has lost important native structural features. This is evidenced in various ways. For instance, such materials do not react in a normal manner with chitin-specific enzymes; they react in vitro, if at all, at rates that are orders of magnitude too slow by comparison to quantitatively assessed in vivo or in situ chitin-degrading processes. Moreover, such preparations often react, albeit slowly, with enzymes such as lysozymes that are specific for linkages not known to occur in chitin. Also, the products of enzymatic digestions of such preparations are not well-characterized or consistent, and the digestions may not go to completion. Microscopic appearance of chitin isolated following established procedures is irregularly compacted (c.f. FIG. 3) and is thus at variance with the well-ordered appearance of chitin strands in situ (c.f. Neville, infra, and Richards, *The Integument of Arthropods*, Univ. Minnesota Press, 1951). In addition, chitin materials prepared according to such techniques may be relatively compact and dense, as reflected in their ability to produce relatively high-concentration suspensions in solvent systems, e.g. the 10% w/v solution used for determining optical rotation.

The extensive, long-standing, and continuing efforts to develop a procedure for preparing commercially useful chitin or derivatives such as chitosan with reproducibly consistent properties attest to the difficulty of the problems encountered. Moreover, existing methods for recovering deproteinized, decalcified chitin yield materials which are often unusable for industrial/agricultural applications. For example, the properties of chitosans derived from such chitin preparations also differ in their behavior with respect e.g. to sequestering of heavy metals which, though generally held to be a typical property of chitosan, nevertheless quantitatively varies widely vis-a-vis a given ionic species when products of successive production runs are tested (Proceed. II Internat. Confer. Chitin/Chitosan, Sapporo, Japan, 1982). Thus, properties of such preparations are neither consistent nor uniform.

It has generally been assumed that such problems are inherent in the structure of the chitin and/or that they arise of necessity in the purification process and, therefore, that the products of demineralization and/or deproteinization are necessarily variable, inconsistent, and generally unreactive.

It is further assumed that "Chitin . . . is not attacked by bacteria and it is difficultly hydrolized [Muzzarelli U.S. Pat. No. 3,635,818];" and that chitin is "extremely resistant to enzymatic action [Dunn U.S. Pat. No. 3,847,897]."

"Chitin does not occur in its pure form in nature but is usually associated with substantial quantities of protein and inorganic salts such as calcium carbonate. . . . It should be noted that chitin is normally found in and associated with living organisms and would be expected to exhibit altered characteristics when removed from the ambit of the biological processes." [Silver U.S. Pat. No. 4,120,933].

Similarly, another researcher has said,

"Because of its insolubility and its close association with other substances, [chitin's] isolation requires the use of drastic methods to remove contaminating substances; these methods probably degrade chitin to some extent." BeMiller (supra).

Attempts to circumvent these problems by utilizing crustacean meal made from cannery waste have also not met with success. According to Peniston [U.S. Pat. No. 4,199,496]:

"In general, shellfish waste meals have limited markets due to their high mineral and chitin content. This limits levels at which... shellfish waste meal can be fed to farm animals and to poultry." and "Chitin is indigestible for poultry and livestock and can cause intestinal irritation. Thus, only the protein [of crustacean waste meal] is of real value as a feed material and the other components of shellfish meal are undesirable diluents detracting from the feed value."

SUMMARY OF THE INVENTION

I have discovered that naturally occurring molecular chitin structures are complex and highly ordered, as well as extremely fragile, and sensitive to many chemical treatments and that existing efforts to remove mineral, protein, and other matter associated with naturally occurring calcium-containing chitins radically alter the native structure. Specifically, native calcium-containing chitins are present in a matrix, parts of which include chitin-protein and protein-protein cross-links. The matrix is heavily encrusted with minerals such as calcium salts, and often includes lipids and coloring material. Once lost, that fine structure cannot be regenerated from chitin that has been altered during the process of separation from its natural environment. Moreover, loss of the native chitin fine structure results in degradation of the tensile strength and other desirable properties of native chitin; loss of the fine structure also results in a dramatic loss of the reproduceability of chitin product characteristics.

In particular, I have discovered how to remove the calcium salts material and the structural protein from naturally occurring (or "native") chitin matrices, to form protochitin polymers which are then intermittently or sparsely esterified, thus replacing the organic (protein) stabilization of fine structure with non-protein or inorganic stabilization. In this way, the fine structure is retained, thus preserving the desirable characteristics of native chitin and improving reproduceability of product characteristics. It appears that the protein covalent links might be replaced with inorganic ester links to maintain the fine structure of the native chitin. The invention features a method in which the naturally occurring chitin matrix is first decalcified; then, it is deproteinized to produce compacted protochitin fibers retaining the fine structure of native chitin. The resulting protochitin is then sparsely esterified by dispersing it in cooled, ester-forming acid to form a colloidal solution in which said native chitin fine structure is maintained, and is not subject to shear. Finally, the sparsely esterified stabilized purified chitin is recovered by precipitation.

The resulting ester-stabilized chitin polymer are water insoluble, uniformly dispersible in suspension, highly elongated relative to their diameter, not subject to shear in aqueous suspension, and hydrolyzed by extra-cellular chitinase produced by an adapted microorganism plated on agar and the ester-stabilized chitin, the hydrolysis being rapid and quantitative. By adaptive I mean that a wild type microorganism such as an Actinomycete, a Vibrio, etc. is adapted to produce extra-cellular chitinase by exposure to native chitin structures as a carbon and nitrogen source. Such an adapted microorganism will clear an agar plate containing 7 mg of ester-stabilized chitin/15 ml of 2% agar such that, within 48 hours at 25° C., a plaque of cleared agar extends at least about 15 diameters of the cloning diameter.

The ester-stabilized chitin polymers are purified in that they have been dissociated substantially from the native chitin's calcium-reinforced protein matrix. The ester-stabilized chitin retains the fine structure (e.g. tertiary and quaternary structure) of native chitin polymers, and therefore the ester-stabilized chitin provides a source of consistently uniform material. A particularly sensitive indication that the ester-stabilized chitin retains the native chitin fine structure is the ability of the ester-stabilized chitin to serve as a substrate for rapid, quantitative recognition by enzymes specific for naturally occurring chitins, including chitinase (EC 3.2.1.14) and chitin deacetylase, and nearly complete lack of recognition of ester-stabilized chitin by enzymes specific for other substrates, e.g. lysozymes. By sparsely esterified I mean that the degree of saturation (DOS), defined as esterifiable sites per 100 sugar residues, is less than 0.05. By fibrous, I mean that the isolated or dispersed chitin is predominantly characterized by relatively large, well organized elongated fibers, for example, thick fibers that are between about 2 and 7 microns in diameter. By dispersible, I mean that the chitin polymers can be readily and uniformly suspended in an aqueous solution. By chitin-specific enzymes, I mean enzymes such as endo- or exo-chitinases or chitin deacetylases which react rapidly and quantitatively with naturally occurring chitins, and mean to exclude enzymes, such as non-specific hexosaminidases or lysozymes, which recognize structurally similar but not necessarily identical glycosidic bonds, and which react slowly, if at all, with chitin that largely retains its natural molecular structure.

Most preferably, the stabilizing ester functions are phosphate or sulfate functions; it is possible that such functions form cross-links between chains of N-acetylglucosamine units, but for purposes of practicing this invention, it is not necessary to know whether such cross-links in fact are formed. The ester functions may also be formate, acetate, or nitrate functions.

The resulting product precipitates in water or aqueous ethanol as an insoluble gel or flocculent precipitate which exhibits substantial solvent regain, another indication that the product retains native chitin fine structure and desirable characteristics. For example, each mg of precipitate is solvated by 0.15 ml or more solvent, e.g. water; thus 5 mg of precipitate contains one ml of solvent. Also by way of example, the wt/wt ratio of chitin/solvent is on the order of at least about 1:100 and preferably at least 1:200. The product is preferably mineral free, as determined by the substantial absence of ash when fully incinerated. The product is also substantially protein free, as determined by the absence of a characteristic tyrosine absorption of light at 280 nm following basic hydrolysis. The ester-stabilized chitin exhibits characteristic circular dichroism spectra indicating ordered structure such as helicity. While ester-stabilized chitin can be dispersed in aqueous solutions, it is not soluble in water; nor is it soluble in more exotic solvents such as dry dimethylacetamide—5% LiCl, trichloroacetic acid, chloralhydrate, or methylene chloride systems used by Austin et al. in U.S. Pat. No. 4,029,727. A dispersal of ester-stabilized chitin preferably can be dried to a clear sheet, as opposed to granules.

A preferred, more detailed statement of the method of producing ester-stabilized chitin includes the following steps:
  I. Native chitin in the form of shellfish waste
  II. Removal of "adventitious protein" (tissue adhering to shell)
  III. Removal of calcium salts
  IV. Removal of "structural protein" (protein bound within the chitin matrix) to form protochitin
  V. Suspension of protochitin in dilute cold ester-forming acid to form a colloid
  VI. Precipitation of ester-stabilized chitin to form an aqueous-dispersible gel having native chitin fine structure In the above sequence, steps II and III may be combined. Also, the decalcified chitin of III can be air dried and crushed to render it more compact for storage. It is particularly important that, once structural protein has been removed, the chitinous material be sparsely esterified to restabilize it by forming sparse preferably inorganic ester bonds. Thus, once native chitin has been deproteinized (i.e., removing structural protein by a technique such as hydrolysis in NaOH), it must not then be subjected to HCl (such as generally is used to remove calcium salts at this rather early stage of chitin purification) or to concentrated $H_2SO_4$ which will destroy the chitin fine structure, by, inter alia, extensive hydrolysis and sulfation. Even when the concentrated $H_2SO_4$ is cooled to 0° C., it is reported that "drastic depolymerization" occurs. *Nagasawa et al. Carbohydrate Research* 18:95–102 (1972). Exposing protochitin to warm acid (e.g. room temperature or higher) even if it is an ester-forming acid such as phosphoric acid, also destroys fine structure.

In preferred embodiments of the method, the temperature of the chitin dispersal medium is kept uniform to within ±1° C. (most preferably ±0.5° C.) throughout the dispersal; the temperature of the dispersal is kept below 8° C.; the dispersal is continued long enough to permit sparse esterification. The duration of dispersal will depend in part on the nature of the raw material used. Chitin obtained from shrimp can be dispersed over a period of 3-24 hours. Lobster chitin dispersal requires more time, e.g. 3-48 or even 72 hours. The protochitin particles that are dispersed preferably are large enough (e.g. at least 1 mm and most preferably at least 3 mm) to permit early manipulation. The dilute acid (such as sulfuric or phosphoric acid) is pre-chilled and added slowly to the aqueous protochitin suspension to a final concentration of less than 95%. Lipids and other non-chitin material (such as coloring material) are removed in the course of the preparation, without steps introduced specifically for this purpose, since such steps frequently are damaging to the delicate chitin fine structure.

Because the resulting ester-stabilized chitin polymers substantially preserve the native chitins structural features, these products provide uniform, reproduceable chitin structures for use in a wide variety of applications discussed elsewhere herein.

These products are particularly useful as a substrate for enzymatic processes, and will perform well in selected chemical procedures. In this, they contrast sharply with existing purified and/or regenerated chitins which exhibit collapse of innate structure by greatly altered densities, greatly altered appearance in light and/or electron microscopic examination, and inability to form uniform suspensions in aqueous solutions and/or to furnish derivatives with predictable properties and/or to serve as substrates for specific enzymatic processes.

The invention thus features the use of the chitin polymers in a number of enzymatic processes: formation of structured chitosan by enzymatic deacetylation of stabilized chitin; use as a benign plant pestacide because its stabilized native structure stimulates growth of Actinomycetes and beneficial fungi whose activity lowers infestation of pests such as nematodes, Fusarium wilt, root knot, etc.; fertilization of plants by enzymatic degradation of the stabilized dispersed chitin polymer to provide a steady, predictable supply of useful (i.e. "fixed") nitrogen without itself being subject to loss by leaching; use as a source of non-protein nitrogen (NPN) and sugar and acetate carbon, i.e. energy as well as NPN, in ruminant, bird, or fish feedstuffs; formation of a nutrient lawn containing the chitin polymer which is used as an indicator to detect chitinase, e.g. to select microorganisms that produce extracellular chitinase; and as a source of ammonia to be trapped and exploited for fertilizer formulations in industrial fermentations, while the residual fructose can readily be industrially fermented to ethanol—a desirable source of energy, e.g. for operating internal combustion engines.

The importance of a process that reproducibly yields a predictable product is illustrated by the use of ester-stabilized chitin as a carbon and nitrogen source for microorganisms that produce chitinases. For example, ester-stabilized chitin can be used to support rapid growth of the nematocidal fungus in a process that otherwise is very slow, as described, inter alia, by McCandliss in U.S. Pat. No. 4,536,207.

Alternatively, ester-stabilized chitin can be used to form a lawn that is quantitatively and rapidly (under 48 hours) cleared by Streptomyces (see FIG. 4). The reliable, rapid degradation by chitinase makes ester-stabilized chitin particularly useful in this assay. More importantly the assay is useful as proof of stabilization of fine structure as described above.

Finally, ester-stabilized chitin can be used as a ruminant feed supplement. Ruminants utilize nitrogenous compounds by microbial fermentation and biosynthesis, e.g. of amino acids, in the rumen. Chitin that is predictably recognized by specific microbial enzymes can furnish non-protein nitrogen for augmenting such relatively incomplete feeds such as hay, especially in winter when a diet of hay alone leads to a negative nitrogen balance in the animal. However, if such enzymatic recognition cannot be assured, chitin cannot be used as a feed, because undigested chitin remaining for more than a few days in the stomach is extremely detrimental to the animal. Thus, processes at present practiced which yield products of uncertain structure and composition are of no commercial value.

Apart from the enzymatic uses specified above, the chitin polymer or chitosan produced from it are generally useful as industrial feedstocks where consistent, predictable properties of native chitin are important. Specific examples of uses proposed for chitin and chitosan include: agents to selectively chelate various metal ions (e.g., for removal of radioactive ions that are products of nuclear fission, to purify metal-working waste water, to reclaim metal waste, or to purify reaction products); paper or fabric additives or finishes which carry dye, repel soil, shrink-proof, etc.; a photographic substrate; adhesives; a leather finishing agent; a formative material for medical membranes; a pharmaceutical carrier for poorly soluble drugs; a blood coagulant; a biodegradable medical filament or fabric; or an adjuvant for arable land to improve tilth while at the same time providing significant usable nitrogen for plants.

The following references disclose methods of using the chitin polymer and chitosan derived from it: Jones U.S. Pat. No. 2,689,244—thickener for paste, adhesive, additive for drilling; Austin U.S. Pat. No. 4,286,087—wound healing; Austin 3,879,377—papermaking, surfactant; Vogler U.S. Pat. No. 2,831,851—blood anticoagulant; Dunn U.S. Pat. No. 3,847,897—thickener, stabilizer in food; Cushing U.S. Pat. No. 2,755,275 blood anticoagulant; Delangre U.S. Pat. No. 2,842,049—photo processing; Wolf U.S. Pat. No. 2,973,274—glycerol ointment; Turner U.S. Pat. No. 3,368,940—purification of biological material; Bornstein U.S. Pat. No. 3,333,744—meat extender; Peniston U.S. Pat. No. 3,533,940—anti-coagulant; Muzzarelli U.S. Pat. No. 3,635,818—metal ion chelating; Bridgeford U.S. Pat. No. 3,689,466—soil repellant; Balassa U.S. Pat. No. 3,914,4130—wound healing; Katz U.S. Pat. No. 3,940,317—isolating lysozyme; Dunn U.S. Pat. No. 4,034,121—food thickener; Slagel U.S. Pat. No. 4,056,432—paper additive; Nieuwenhuis U.S. Pat. No. 4,156,647—wastewater treatment; Casey U.S. Pat. No. 4,068,757—powder for surgical gloves; Capozza U.S. Pat. No. 4,074,713—surgical elements; Muralidhara U.S. Pat. No. 4,293,098—animal feed additive; Silver U.S. Pat. No. 4,120,933—removal of radioactive waste; Schanze U.S. Pat. No. 4,357,358—animal feed additive. The above patents are hereby incorporated by reference.

Other features and advantages of the invention will be apparent from the following description of the preferred embodiment and from the claims.

DESCRIPTION OF THE PREFERRED EMBODIMENT

I will next briefly describe the drawings of the preferred embodiment.

Drawings

I. The Native Chitin

Virtually any recognized natural source of calcium-bearing chitin serves as an appropriate starting material for production of purified stabilized chitin. Crustacean shells and whole crustaceans (e.g. krill) are among the most plentiful sources of such native chitin.

II. Preparation of Stabilized Chitin

A. Removal of Calcium And Adventitions Protein

Figure 5:
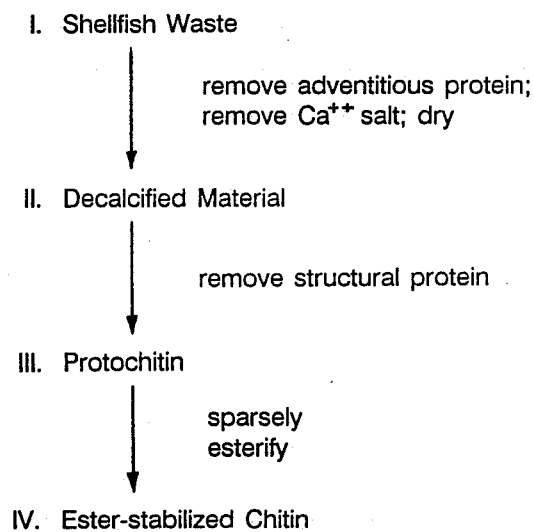
FIG. 5 is a flow diagram showing the steps in the preferred process of preparing ester-stabilized chitin from native chitin.

As shown in FIG. 5 and example 1, the shellfish waste (I.) is first treated to remove "adventitious" protein, that is, the residual shellfish meat that is attached to shell fragments. I use the term "adventitious protein" to distinguish it from structural protein that is covalently or otherwise bound to the native chitin fibers. Removal of structural protein is described below. It is useful to be able to store the resulting material, and to be able to mill and/or crush it, so that the material can be transported to centralized processing facilities. This allows storage at any convenient ambient temperature, or transport to processing plants, without spoilage, and at greatly reduced weight.

In one process (shown in FIG. 5) the shellfish waste is treated with cold, dilute (e.g. about 0.5–1 N) HCl to arrest spoilage, remove calcium salts (largely $CaCO_3$), and adventitious protein at the same time. The resulting material (II.) is brittle after drying and can be reduced readily to pieces of convenient size for storage, deproteinization and dispersal.

In an alternative method (example 3, below) adventitious protein can be removed first, followed by milling and then decalcification. Specifically, intact chitin-bearing structures are initially preserved by boiling in water or rinsing with an antioxidant solution, and then air dried for storage or transport. The structures are then mechanically disintegrated by cutting, milling, or grinding to a uniform size for further processing; this step may equally well be performed after decalcification, as discussed above. Calcium (present largely as $CaCO_3$) is removed by treatment with dilute hydrochloric acid, EDTA, or enzymatic action.

In either process, if HCl is used for decalcification, then decalcification must be done before deproteinization (described below) because any exposure of the deproteinized prestabilized chitin to HCl or other non-esterifying acids such as $HClO_4$ will irreversibly destroy its native structure.

Using either process, the resulting material is a decalcified material (II in FIG. 5).

B. Deproteinization

Following decalcification, structural protein, lipids, and coloring material may then be removed using boiling dilute NaOH or specific enzymes. Once these materials are removed, the innate chitin structure is vulnerable to collapse, particularly if exposed to non-esterifying acids and/or oxidizing chemicals. Such collapse is irreversible and extremely detrimental, in that collapse renders the material of unpredictable structure, molecular size, and utility in various industrial applications; it dramatically reduces the consistency and quality of performance of the isolated material in most applications. The collapse can be demonstrated in various ways, but a particularly sensitive test is the failure of chitin specific enzymes to recognize collapsed material.

In sum, it is desirable to maintain the decalcified deproteinized chitin in a relatively neutral environment (e.g. between pH 5 and 8, or, optimally, in the dry state at any convenient ambient temperature) until the next step (the dispersal step) is performed. I have desiqnated the resulting material "protochitin" (III. in FIG. 5) because the native chitin structure is potentially present, but in an unstable form, which is not suitable as an enzyme substrate, but which can again be stabilized by careful treatment as set forth in C, below. It is particularly important at this stage to avoid exposure to non-esterifying acids (e.g. HCl) and/or to strongly oxidizing conditions (e.g. permanganate solution).

C. Stabilization and Dispersal of Purified Chitin

Extreme care must be exercised to disperse the resulting decalcified and deproteinized chitin to avoid damage to its structure. Specifically, the temperature of the dispersion, the final concentration and rate of addition of the acid, and, most importantly, the anion of the acid used, must be controlled with precision. Acid dispersal is required so as to create a substrate that is rapidly attacked by chitin-specific enzymes; mere milling is insufficient to bring the macromolecular assemblies to a physical state which enzymes can readily attack.

The acid used must be one capable of esterifying the chitin. Most preferably, the acid should be a phosphate or sulfate containing acid such as $H_3PO_4$ or $H_2SO_4$. Without being bound to a theory, it is possible that these acids are multi-ester forming (i.e., their corresponding bases have more than one oxygen available for ester formation). If these oxygens bond to separate chitin fibrils, they can form a cross-link between them to aid stabilization.

Stabilization by ester forming acids remains effective so long as the stabilized chitin is not subjected to conditions that hydrolyze the ester bonds. If those bonds are hydrolyzed (e.g. by subjecting the chitin to prolonged exposure to acidic conditions, above 25% (V/V) or to high heat together with highly basic conditions as customarily practiced in chemical deacetylation of chitin during the manufacture of chitosan), the native chitin structure collapses irreversibly.

During dispersal, if the acid concentration is too great relative to the water concentration, an apparent over-esterification occurs resulting in a product of very low density and no discernible practical value. If the acid concentration is too low, and/or rate of acid infusion occurs at too slow a rate, the bonding (cross-linking) may not keep pace with dispersal, leading to collapse of native structure, or dispersal may fail to occur. Excessive temperature during dispersal, even if only in limited locations, or acid contact beyond what is required for dispersal, again destroy the native chitin structures as well as reducing yield of insoluble fibers, presumably through excessive chain shortening. Finally, exposure of the material to strong oxidizing agents such as ozone, $H_2O_2$, or permanganate (e.g. as often done to remove color-forming material) must be avoided to prevent degradation of chain length as well as destruction of innate structure and sugar monomers.

In sum, during dispersal, the temperature of the dispersal medium should be controlled throughout the medium to within at least 2° C. and most preferably 1° C., and the dispersal medium should be restricted to aqueous ester-forming acids in suitable intermediate and final concentration. To avoid localized "burns" from excessive temperature or acid concentration, the protochitin must be well wetted with water and the acid should be pre-cooled and added slowly with stirring to the precooled stirring suspension of crushed or milled protochitin in the corresponding amount of water.

The preferred temperature of the pre-cooled acid, and throughout the dispersal medium, is below 8° C. and most preferably below 4° C.; the temperature should be greater than −5° C. Initially, the acid concentration is below about 80% (V/V), and most preferably is below 20%. Acid is added up to a final concentration of between 25 and 90% (V/V) and is most preferably less than 70% (V/V) because yield is significantly reduced above that level. The time of exposure of the chitin to the dispersal acid is between 3 and 48, or up to 72 hours for lobster chitin, and most preferably less than 24 hours for shrimp chitin.

After dispersal and esterification, the stabilized product forms a colloidal solution in the esterifying acid. The product is precipitated in a large volume of cold rapidly-stirred water, alcohol, or a similar organic solvent which optionally is admixed with water, and harvested. Acid is removed by repeated water rinses, and the product is preserved by adding azide, unless it is to be used in manufacture of comestibles. The product is preferably handled in a sterile environment to avoid contamination by chitinase-forming microorganisms that could degrade the product.

Figure 1:
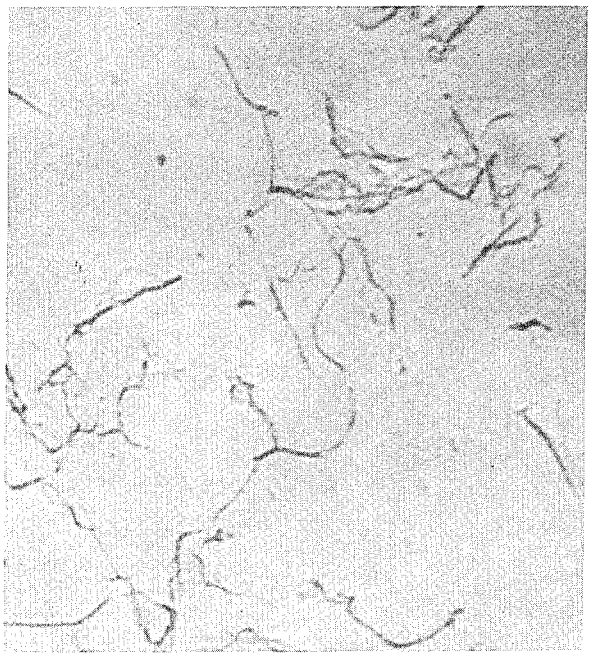
FIG. 1 is a photograph (400x) of stabilized shrimp chitin.
Figure 2:
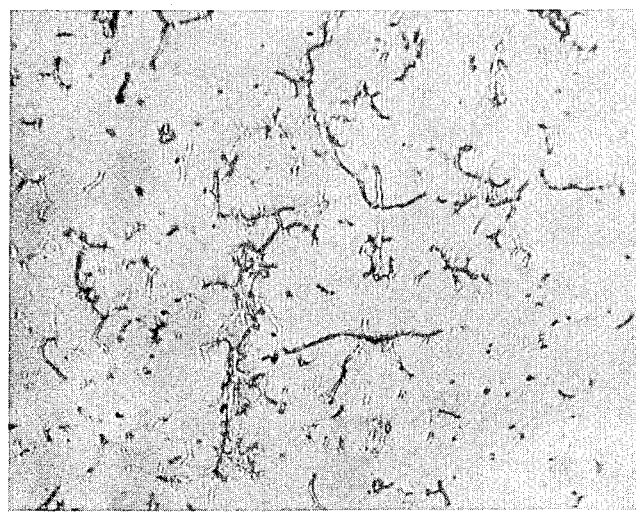
FIG. 2 is a photograph (400x) of stabilized lobster chitin.

FIGS. 1 and 2 are 400X photographs of sulfate stabilized sparsely esterified shrimp and lobster chitin, respectively, prepared according to the described method.

D. Example Of Laboratory Chitin Preparation

1. Example 1

Five pounds wet crab waste is immersed in six liters of 0.58 N HCl at 4° C. and kept submerged for three days with occasional agitation. Adventitious protein (i.e. incompletely removed "meat") is then mechanically separated from the decalcified carapaces which are air-dried overnight and ground (into coarse particles (larger than 1 mm diameter, 3–20 mm preferred). The resulting material (about 63g) is freed of structural proteins by boiling in five changes, each of 600ml 1N NaOH. Protein solubilization is monitored by inspection of the supernatant base spectrophotometrically at 280 nm (the molar absorption coefficient of a particular protein of 80,000 MW is $5.6 \times 10^4$). The supernatant from the fifth batch of NaOH appears free of protein by these means. The solid residue weighs approximately 38g; it is designated "protochitin" or "compacted native chitin" and can be shown to contain latent fibers. It is rinsed with several changes of water and stirred in 2300ml 70% phosphoric acid at 2° C. for 48 hours. At that time, the optically clear colloidal phosphate-stabilized chitin solution has a viscosity of 3 min. 50 sec. (at 22° C. and a concentration of 12 mg stabilized chitin per ml) compared to 1 min. 22.1 sec. for 70% phosphoric acid at the same temperature. Dilution of the 2300 ml colloidal solution in 9l ice-cold aqueous ethanol (1:1, v/v) gives a copious flocculent precipitate. The 9l are further diluted with water to a total of 20:1. The gelatinous phosphate-stabilized crab chitin is filtered off, resuspended in 20l water, and filtered again. Yield is about 18g fibrous crab chitin; solvent regain is 1cc per 5mg phosphate-stabilized crab chitin.

2. Example 2

Decalcified deproteinized shrimp chitin is suspended in water at 2° C. and phosphoric acid is added dropwise with vigorous stirring until the phosphoric acid concentration is 67%. The colloidal solution of phosphate-stabilized shrimp chitin (PSSC) is initially cloudy but clears in less than 1 min. when the phosphoric acid concentration is made to 70%. The PSSC is precipitated by dilution in 10l water and filtered, then resuspended in an equal volume of water and again filtered. The PSSC forms a stable suspension in water when present at a concentration of 5 mg/cc or greater.

3. Example 3

Shrimp chitin, when decalcified by cool dilute HCl and deproteinized by repeated 30 minute boiling in 1N NaOH, is crumbly and easily disintegrates. In a typical experiment, 4 gm of such material is suspended in 100 ml water at 4° C. while 100 ml conc. $H_2SO_4$ at 4° C. is added to the stirring suspension at the rate of 1 drop/30-sec. When all chitin has dispersed, the viscous solution is precipitated in rapidly stirring 50% aqueous ethanol at 4° C., harvested in the centrifuge, and washed to pH 5. After taring, a suspension of 6 mg/ml is prepared in 0.1 M phosphate-acetate buffer (pH 6.5); the buffered substrate is preserved with 0.02% azide or other similar preservative or mold-inhibiting substance, or, before or after buffering, the substrate may be freeze-dried for storage.

The specific methods outlined in the above procedure are not intended to be restrictive with respect to modifications that may be dictated by upscaling to industrial production; for example it may be desirable to carry out the mixing procedure during the dispersal by sparging. Precipitation by addition of precipitant to the dispersal medium (rather than vice versa) may give better results in larger-scale operation. The precipitated solid may be harvested by a "sluicing" procedure which might combine continuous washing and harvesting. Alternatively, harvesting might be accomplished by filtration through finely woven fibers.

III. Product Characterization

A. General

The stabilized chitin resulting from the above process is substantially free of non-chitinous material, yet it substantially preserves the structure of the native chitin By "substantially free of non-chitinous material," I mean that the product has less than (by weight) 2% amino acid and negligible ash content when subjected to flame ashing and is more than 98% chitinous material. This contrasts with chitins prepared by excessively harsh procedures, such as use of elevated temperatures or strong acids which destroy the naturally occurring fine structure, often trapping amino acids and/or ash within the resulting dense mass of material. By the phrase "substantially preserves the structure of the native chitin" I mean that the product in question appears to retain fibrous structure that is visible in the light microscope and may preexist in similar form in the deproteinized carapace; I also mean that it is recognized by enzymes that are specific for native chitin, *Streptomyces* chitinases and other specific hydrolytic enzymes, e.g. from wheat germ, or *S. marcescens;* such enzymes react in variable fashion, or not at all, with substrates such as chemically collapsed or otherwise structurally damaged or altered chitin. Stabilized chitin is also unreactive with enzymes specific for other materials of known structure; for example, it is not susceptible to attack by lysozyme. More specifically, the stabilized chitin exhibits normal kinetic behavior with chitin-specific enzymes: it reacts at rates that are comparable to rates of in vivo chitin reactions such as rapid enzymatic hydrolysis typical of breakdown of shed carapaces, e.g. in aquatic environments, and generally gives linear product generation with all chitinases examined. Further, the kinetics of the reaction can readily be characterized (e.g. as to reaction order and mechanism) by standard techniques. In contrast, structurally collapsed chitin or chitin derivatized so as to be made water-soluble will be degraded slowly and abnormally by non-specific hexosaminidases, or may even be attacked by lysozymes and/or commercial preparations of beta-glucosidase, but either not at all, or else very slowly, by chitin-specific enzymes. Rates of degradation such as those listed above are so slow, and the kinetics of such reactions are so abnormal, that they cannot be indicative of true in vivo reactions.

Even labeled products sold or prepared in the laboratory as substrates for testing alleged chitinase activity reflect abnormal enzyme kinetics. See Molano et al. (1977) Anal. Biochem. 83: 648–656.

The chitin-specific enzymes which recognize the stabilized chitin polymer to the exclusion of structurally altered chitin derivatives include all enzymes known to recognize chitin in its naturally occurring form such as true chitinases (not non-specific hexosaminidases or lysozymes) and chitin deacylases. Those enzymes include chitinases (EC 3.2.1.14), such as those obtained from Streptomyces cultures and available from Sigma Chemical Co., St. Louis, Mo., and other commercial sources; also included are enzymes from the moth *Manduca sexta,* or digestive tracts of arthropod-eating vertebrates and invertebrates. Other chitin-specific enzymes include the chitin deacetylases such as those discussed below.

Microscopic examination of the product resulting from the method of chitin purification attained above reveals fibrous structures. Specifically, many highly elongated fibers are observed whose diameter varies by about 2 microns about median values of 2 to 6 microns; median diameter variation appears to be in the first instance species-specific, by which I mean that e.g. lobster chitin fibers tend to be thicker on the average than shrimp chitin fibers. The fibers are readily dispersible into suspensions of statistically uniform particle suspensions. They appear to correspond to singles or multiples of protein-stabilized fibers seen as integral parts of the native chitin structure in electron micrographs at very high magnification [see e.g. Neville, Biology of the Arthropod Cuticle, pp. 170–174 Springer Verlag, New York 1975]. Thin fibers in tightly coiled form are occasionally visible in microscopic examination of stabilized chitin preparations.

If the integrity of chitin chains in properly prepared protochitin is in part destroyed e.g. by brief exposure of the protochitin to cool dilute $KMnO_4$, fibers can subsequently be sheared off in a Warning blender that in microscopic appearance resemble ester-stabilized chitin fibers. The ester-stabilized fibers I isolate are the product of low-temperature physicochemical processes leading, via orderly formation of a colloidal solution of initially intact protochitin in cold dilute ester-forming acid, to precipitation of characteristic ester-stabilized chitin fibers by further dilution of the colloidal solution e.g. by water or aqueous ethanol. Although convenient for handling purposes, mechanical disintegration by grinding or milling of chitinous structures is not, as such, required at any stage of preparation of the dispersible native ester-stabilized fibers here disclosed.

Without being bound to a particular theory, the thick fibers are believed to arise chiefly by cross-linking of thin, pre-existing fibers occasionally visible in tightly coiled form by microscopic examination of stabilized chitin preparations. It is possible that the cross-linking is achieved by polybasic ester functions as previously described. The thin fibers may correspond to the fiber structure seen as integral parts of the native chitin structure in electron micrographs at very high magnification [see, Neville, Biology of the Arthropod Cuticle, e.g., pp 170-174 Springer-Verlag, New York 1975].

Figure 3:
FIG. 3 is a photograph (400x) of collapsed crab chitin.

These fiber structures can be altered, e.g. mechanically, in predictable ways, and such alterations affect, again predictably, their digestion by enzymes and other properties in ways indicative of structural alterations. The collapse of such thin fibers releases short (water-soluble) segments of chitin thought to arise from artifactual intra-fibrillar chain scission. Insect molting fluid chitinase, having both endo- and exochitinase activity, digests a mixture of thick and thin fibers completely; commercially obtained Streptomyces chitinase from Sigma Chemical Co., which in some preparations retains little or no endochitinase activity, may cleanly digest only the thick fibers, while the (collapsed) thin fibers are not attacked at all. These facts are easily established by examination with a light microscope. If, however, collapsed chitin, e.g. collapsed thin fibers or chemically collapsed material as shown in FIG. 3, is exposed to a commercially available preparation of "beta-glucosidase" (which is not supposed to have any chitinase activity at all), the collapsed material is attacked at a fairly rapid rate, with the thick fibers remaining intact.

For example, commercially available chitin "purified" by means generally practiced is often microscopically seen to be collapsed; its state of subdivision does not permit preparation of uniformly dispersed suspensions; it may release soluble oligomers non-enzymatically during attempted enzyme assays due to intrafibrillar chain scission occurring in consequence of faulty processing from the original chitinous carapace; and it is not fully recognized by chitin-specific enzymes in that residues, even those which have been assembled from chitin that has suffered initial destruction of fine structure with chitin-specific enzymes in that substantial residues, even those which microscopically resemble fibers but which have been assembled from chitin that has suffered initial destruction of fine structure with subsequent partial "regeneration", remain undigested for substantial periods (days, if not indefinitely).

The ester character of the product is demonstrated in several ways: (1) When radio-labeled ester-forming acids are used, a non-dialyzable quantity of radioactive tracer becomes incorporated into the product isolated. (2) All ester-forming acids examined permitted isolation of fibrous chitin, while several non-ester forming acids did not. (3) Direct analysis for covalent bonding of ester functions showed that the inorganic esters became available for analysis only with complete hydrolysis of the stabilized chitin.

The product is particularly characterized in its relatively non-dense and uncompact nature, as evidenced by its behavior in suspension and solution in solvent systems, in that only relatively small amounts of product can be suspended or dissolved, in comparison, e.g. to the dense collapsed preparation described by Austin (e.g. in U.S. Pat. No. 4,286,087). It thus resembles the original protein-stabilized native fibers in which, however, inorganic ester functions covalently bound play the role of stabilizing protein functions; their lower bulk facilitates enzymatic and chemical reactions.

B. Specific Tests For Chitinase Activity

I have developed or adapted a variety of tests for measuring or detecting the various aspects of chitinase activity encountered using native stabilized fibrous chitin, and these will now briefly be described.

1. "Clearing assay." In this test, one quantitates the light scattered by suspended chitin particles. The amount of light scattered can be accurately measured as the ratio of incident light at 350nm wavelength that is not received by the phototube in the spectrophotometer. This ratio is highly sensitive to particle size and, within experimentally determined limits, is linearly related to it. "Clearing" i.e. the reduction in the ratio of light scattered, serves (with proper controls) to quantitate the degree of reduction in particle size resulting from the activity of endochitinase, i.e. enzymatic activity scissioning chitin particles, presumably at random, into shorter lengths. By contrast, the clearing test gives far less useful results when only exochitinase activity is present, i.e. when the activity to be measured consists entirely in the serial removal of short lengths, most typically disaccharides, from either the reducing or the non-reducing ends of the polysaccharide.

The reaction set-up for the clearing test is as follows:
In 2.0 ml final volume, the following quantities of reactants are assembled:
50mM phosphate acetate buffer (pH 6.5)
1mM $CaCl_2$
2.4 mg chitin/milliliter
0.1 ml enzyme/milliliter (from a stock solution containing 4.0 mg solid per milliliter).

The reaction is initiated by addition of enzyme and incubation at 37° with stirring is continued for as long as desired. To take a reading, the mixture is poured into a cuvette; it is then immediately returned to the test tube and the incubation continued.

2. Colorimetric tests for N-acetyglucosamine.

Such a test is set up with the same reactant concentrations as given for the clearing test. Three test tubes containing 1 ml of total reaction mixture each are prepared for each experimental point desired. To assure the proper zero value, each reaction mixture is pre-stirred at 37° for a minimum of 5 minutes. Enzyme (e.g. Streptomyces chitinase from Sigma Co.) is then added. A zero-time sample is obtained by spinning one of each triple set of tubes at 12,000xg in a microcentrifuge and sampling 0.4 ml of the supernatant. The remaining tubes from each set are incubated with continual stirring at 37° for 30 minutes, at which time 0.4 ml samples are taken in the same manner.

To each 0.4 ml sample, 0.1 ml excess hexosaminidase solution is added and the samples are incubated at 37° for a further 15 minutes to convert any oligomeric products to the monomer N-acetylglucosamine. Duplicate sub-samples of 0.1 ml each are then taken and the colored adduct is developed quantitatively by a somewhat modified version of a well-known procedure (Reissig et al. (1955) J. Biol. Chem. 217: 959-966).

3. Qualitative Detection of Chitinases.

The following two tests may be used to detect the presence of chitin-specific enzymes using a stabilized native fibrous chitin.

Figure 4:
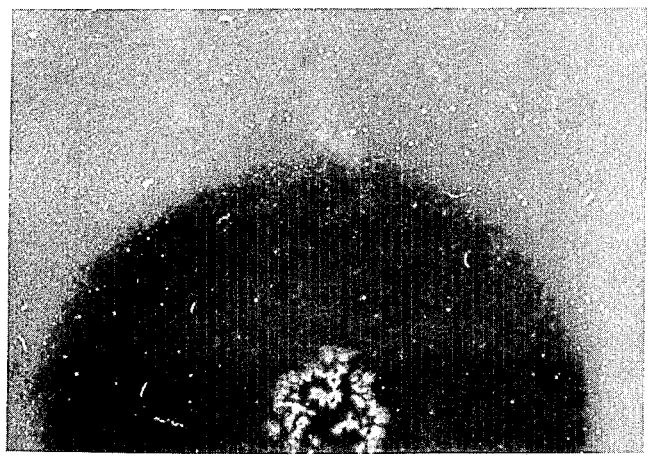
FIG. 4 is a photograph (9x) of a chitin-agar lawn exposed to extracellular chitinase exuded by the cells shown during, and as a result of, their growth as colonies.

(a) Chitin-agar plaque test. A chitin-agar "lawn" is prepared as follows: 7 mg of stabilized native fibrous chitin is suspended in 15 ml of a hot sterile solution containing 1.8 gm agar dissolved in 100 ml of water or buffer. The hot suspension is poured into a sterile petri dish of suitable size. The layered suspension sets quickly at room temperature and may then be used to plate out microorganisms. Any such organism adapted for the formation of extracellular soluble chitinase will be able to form colonies on the chitin-agar; as the colony grows, the soluble chitinase diffuses outward from it so as to furnish necessary nutrients for further growth of each colony. This leads to the rapid (within no more than 24–48 hours) formation of a clear "halo" or "plaque" around the colony which is easily distinguished from the uniformly cloudy chitin suspension forming the original lawn (see FIG. 4).

(b) "Abklatsch" test. This is a more general test for carbohydratases and works particularly well for cell-free enzymes. A carbohydrate-agar lawn is again prepared in a petri dish as in the previous procedure. The chief requirement for this test, however, is that the carbohydrate be either very large (as e.g. chitin or chitosan) or else non-reducing (e.g. sucrose or trehalose). The enzyme to be tested is spotted on the set agar lawn, the agar is covered with a piece of moistened filter paper, and the assembly is incubated for a few hours to overnight. The filter paper is removed and airdried. Any small, hence diffusible reducing sugar resulting from enzyme activity will have diffused, both into the agar (where it is of course lost) and into the filter paper where it can be detected by the alkaline silver method for reducing sugars (Trevelyan and Harrison, Biochem, Jour. 50: 298–303).

4. Uses of radioactive label. I utilize labeled compounds to determine enzyme recognition of stabilized native fibrous chitin. If a radiolabeled chitin precursor, e.g. N-acetylglucosamine, is injected during the time of maximal rate of synthesis of new cuticle chitin, i.e. a few hours prior to ecdysis, labeled chitin may be obtained from various arthropod sources. If, for example, such a chitin bears label only in the N-acetyl group, suspected deacetylases may be tested for by comparing solubilized label to label that continues to remain with the insoluble residue even after many washings. In this manner, extracts from both *Rhizopus pseudochinensis* and *Mucor rouxii* were shown to remove 25–30% of label within 24 hours. If the sugar is labeled in the ring either by $^{14}C$ or non-exchangeable $^{3}H$, appearance of acid soluble label readily identifies the presence of chitinase activity. Another manner of introducing label is to use radiolabeled sulfur or phosphorus in the anions of the esterifying acids; such label is used to show directly that acid-dispersed stabilized chitin contains covalently bound ester functions, since label will be released only following (complete) hydrolysis of the labeled material.

5. Deacetylation. There are several methods for verifying recognition of native chitin substrate by deacetylases which yield chitosan [See IV. A. below]. One of the gross behavior patterns by which chitosan is distinguished from chitin is in a rather coarse colorimetric behavior; a more reliable test consists in dissolving any chitosan that may have formed in 3% acetic acid, in which chitin is wholly insoluble. A third test involves the use of chitin labeled in the acetyl group. Chitinases and chitosanases are different enzymes. By all the latter tests, chitosan retaining its chitin-like molecular architecture was produced from stabilized native fibrous chitin by specific deacetylases.

6. Other Tests. Still other tests were used to characterize the purity of the native fibrous chitin; those tests included: conventional and/or radiolabel tests with respect to protein content, sulfate content, amino acid content, ash present, and/or phosphate content of various preparations.

Example

The following example demonstrates a method of establishing that a particular chitin product is rapidly and quantitatively recognized by a chitin-specific enzyme.

Reaction mixtures are prepared containing the following in a total volume of 1.0 ml:
2.5 mg chitin
50 mM phosphate-acetate buffer (pH 6.5)
1 mM $CaCl_2$.

Reaction is initiated by addition of 10 microliter Manduca molting fluid; this can most advantageously be obtained by tapping pharate pupae at the proper time, and quickly freezing it in the presence of phenylthiourea to prevent melanin formation.

The reaction mixtures are stirred continuously in a 37° C. waterbath. Activity is then measured as the absorbance difference in Morgan-Elson color, developed in 0.1 ml aliquots sampled at 5 minutes and 15 minutes of incubation time. Average activity measured is about 1 milligram of N-acetylglucosamine produced per minute per milliliter of raw molting fluid. As an indication of the previous lack of suitable substrates for chitin-specific enzymes, 1 unit of chitinase activity is defined in the 1983 Sigma Chemical Co. catalog as the production of 1 milligram N-acetylglucosamine equivalent in 48 hours, with 2–3 units claimed per milligram of solid for the Streptomyces chitinase sold commercially by this company. With stabilized chitin, this same enzyme preparation can be shown to possess about 19 units per mg solid, while 1 ml raw Manduca molting fluid in these terms might contain in excess of 250,000 units. I consider reaction with a chitin-specific enzyme under the above conditions rapid, quantitative, and specific, if N-acetylglucosamine color that develops with a 0.1 ml subsample gives an appreciable rate of increase as a result of enzyme action (see section III.A.2, above) within 10 to 30 minutes. By "appreciable," I mean a change in absorbance of light at 585 nm of a minimum of 0.100 absorbance units; by "specific" I mean product generation that is linear with respect to time. A clearing test would be required to establish that the enzyme reaction is quantitative; under the conditions described for this assay, an opaque suspension of stabilized chitin would clear completely in under 1 hour.

The above-described clearing test (III.B.1) and colorimetric test (III.B.2) were performed using commercially available (Sigma) *Streptomyces* chitinase on the following three substrates:

(1) stone crab chitin that had been alternately decalcified (1 N HCl, 1 hour at room temperature) and deproteinized (2 boilings in NaOH), after which those procedures were repeated before acid dispersal. The resulting material, as shown in FIG. 3 (400x), is substantially collapsed into a dense mass lacking well-defined fine structure;

(2) chitin prepared according to the procedure in U.S. Pat. No. 4,286,087 for "reorganizing" chitin into a "microcrystalline" form by dissolving commercial crustacean chitin, grade B, from Calbiochem-Behring in 85% $H_3PO_4$ and 2-propanol; and (3) native stabilized fibrous shrimp chitin prepared by the method of the invention described above. As shown in FIG. 1, the resulting product was a dispersal of stabilized chitin fibers.

The "collapsed" and "regenerated" chitin (Nos. 1 and 2, above) did not react to completion and reacted far more slowly than the native stabilized shrimp chitin, particularly with batches of chitinase having predominantly exochitinase activity.

IV. Use

Generally, the stabilized chitin polymer can be used in any of a large number of ways listed above. Specific uses are as follows.

A. Deacetylation

Chitin has a substantial percentage of its sugar groups N-acetylated; many of the uses described above are applicable to chitosan, which is largely deacetylated. The ability of stabilized chitin to serve as a suitable substrate for chitin-specific enzymes enables enzymatic production of stabilized chitosan from stabilized chitin.

Specifically, deacetylases obtained from the following species can be used to enzymatically deacetylate stabilized chitin:

*Rhizopus pseudochinehsis; Rhizopus oligosporus;* and *Mucor rouxii.* Specifically, cell extracts can be used. A reduction in acetylation by 25–30% from an initial acetylation of about 90% (e.g. from about 90% to 65%) will yield a preparation within the range of maximal chitosanase activity.

Chitosans produced enzymatically from stabilized chitins will have predictable and reproducible properties; for example, a particular formulation will sequester specific heavy metal ions in predictable reproducible fashion.

B. Nitrogenous Soil Adjuvant and Fertilizer

Chitinases degrade stabilized chitin to oligomers or monomers of N-acetylglucosamine; further degradation by microbial enzymes into e.g. ammonia has long been known. [See, for example, Davidson, E. A., "Metabolism of Amino Sugars", The Amino Sugars (Balasz et al., Eds) Vol. IIB pp. 1–44 (New York: Acad. Press, 1966)]. It has also long been established that chitin, like other polysaccharides, tends to take up water because of the affinity of free hydroxyl groups for water molecules. Thus, incorporating stabilized chitin into soil can serve several purposes: it can improve tilth, and can also serve as substrate in the slow release of "fixed" nitrogen in a form either directly assimilable by plants, or to be taken up by plants following microbial oxidation, e.g. to nitrate. Use of stabilized chitin for this purpose can also be very advantageous because of its total insolubility in all aqueous solutions one might expect to find in soil. Still another advantage to crop plants would accrue from the fact that chitin tends to support growth of soil actinomycetes which help to keep down plant parasites, at least in part by exuding antibiotics.

It has been estimated that proven reserves of natural gas in the United States will be exhausted by 1990. Natural gas forms the industrial feedstock for the nitrogenous fertilizer industry; use of stabilized chitin could thus fill a gap that would otherwise have to be filled by expensive imports.

C. Ethanol Production

As described above, stabilized chitin can serve as feedstock in well-understood industrial microbial fermentations. Fixed nitrogen can be trapped as chitin is degraded, first to N-acetylglucosamine and then to fructose. The latter can then serve as feedstock for the production of ethanol, a clean and efficient energy source, e.g. for internal combustion engines. In short, the native stabilized fibrous rhitin thus will serve as a vast source of energy from renewable biomass.

D. Feed Supplement

As described above, the native stabilized fibrous chitin can be added to feed of ruminants (or other animals, such as commercially raised birds or fish) to serve as both a nitrogen source and an energy source by providing acetyl groups, fructose monomers, and nitrogen in assimilable form. The stabilized chitin slurry (or dried components thereof) can be combined with conventional feed. The above-described enzymatic tests can be used to determine the nature and presence of enzymes which will consistently and rapidly digest the stabilized chitin. Knowledge of the stoichiometric composition of the chitin can be used to determine, together with the needs of the animals in question and the amount of other feed used, the amount of chitin to add to the feed.

Other embodiments are within the following claims.

I claim:

1. Ester-stabilized chitin fibers, purified from a naturally occurring calcified chitin/protein matrix, said fibers being:
   (a) water insoluble;
   (b) uniformly dispersible in suspension;
   (c) sparsely esterfied with an ester selected from the group consisting of sulfate, nitrate, phosphate, and formate;
   (d) highly elongated relative to their diameter;
   (e) not subject to shear in aqueous suspension;
   (f) hydrolyzed by extracellular chitinase produced by an adapted microorganism plated on agar and said ester-stabilized chitin, said hydrolysis being rapid and quantitative;
   (g) substantially mineral free, yielding substantially no ash when flamed; and
   (h) substantially free from protein upon hydrolysis.

2. The chitin fibers of claim 1 wherein the degree of ester saturation of said fibers is less than 0.05 per esterifiable sites per 100 sugar residues.

3. The chitin fibers of claim 1 wherein said esterification occurs so as to replace protein-chitin bonds of said naturally occurring chitin and thereby preserve the fine structure of said naturally occurring chitin.

4. The ester-stabilized chitin fibers of claim 1 wherein said fibers are elongated and have a diameter of 2–7 microns.

5. The ester-stabilized chitin of claim 1 wherein said chitin is substantially free from non-chitinous material.

6. The ester-stabilized chitin fibers of claim 1 characterized by at least 100-fold (wt:wt) solvent regain in aqueous solvent.

7. The ester-stabilized chitin fibers of claim 1 wherein the fibers are sparsely esterified with phosphate ester functions.

8. The ester-stabilized chitin fibers of claim 1 in which said fibers are sparsely esterified with an ester selected from the group consisting of sulfate, nitrate and phosphate.

9. A chitin product comprising ester-stabilized, aqueous insoluble, aqueous dispersible chitin fibers from a naturally occurring calcified chitin/protein matrix, said chitin product being produced by the process of,
   providing said naturally occurring chitin matrix,
   first decalcifying said naturally occurring chitin matrix under aqueous acidic conditions, to be substantially mineral free, yielding substantially no ash when flamed, then deproteinizing the decalcified chitin under aqueous basic conditions, to produced compacted purified chitin which retains fine structure of said native chitin, and which is substantially free from protein upon hydrolysis, then dispersing the decalcified, deproteinized chitin in a chilled, dilute aqueous ester-forming acid to form a colloidal solution in which said native fine structure is maintained, and is not subject to shear, said acid being selected from the group consisting of nitric, sulfuric, phosphoric, and formic acids, and precipitating ester-stabilized purified chitin fibers.

* * * * *